United States Patent [19]

Albert et al.

[11] Patent Number: 4,734,526

[45] Date of Patent: Mar. 29, 1988

[54] FLUORIDATION AGENT FOR ORGANIC COMPOUNDS, ESPECIALLY ACETYLENIC COMPOUNDS, THE PROCESS FOR THEIR PREPARATION AND THEIR USE IN ADDITION OR NUCLEOPHILIC SUBSTITUTION REACTIONS

[75] Inventors: Patrice J. Albert; Jack Cousseau, both of Angers, France

[73] Assignee: Universite d'Angers, Angers, France

[21] Appl. No.: 848,372

[22] PCT Filed: Jun. 27, 1985

[86] PCT No.: PCT/FR85/00175

§ 371 Date: Apr. 11, 1986

§ 102(e) Date: Apr. 11, 1986

[87] PCT Pub. No.: WO86/00294

PCT Pub. Date: Jan. 16, 1986

[30] Foreign Application Priority Data

Jun. 27, 1984 [FR] France ................................. 84 10137

[51] Int. Cl.$^4$ ............................................. C07C 87/30
[52] U.S. Cl. ........................................ 564/282; 564/291
[58] Field of Search ................................. 564/291, 282

[56] References Cited

U.S. PATENT DOCUMENTS 3,152,073 10/1964 Morton ................................. 564/291
3,388,131 6/1968 Erlangen et al. ................... 564/282

FOREIGN PATENT DOCUMENTS 1435770 3/1966 France ................................. 564/291

OTHER PUBLICATIONS

Domijan et al., Inorganic Chem., vol. 8, #7, pp. 1534–1535, (1969).
Bensadat et al. (I), Chem. Abst., vol. 93, #238946h, (1980).
Bensadat et al. (II), Chem. Abst., vol. 95, #79526u, (1981).
Alieu et al., Chem. Abst., vol. 79, #91647m, (1973).
Domijan, Chem. Abst., vol. 75, #157602u, (1971).

*Primary Examiner*—James H. Reamer
*Attorney, Agent, or Firm*—Cushman, Darby & Cushman

[57] ABSTRACT

Agent for the fluoridation of organic compounds having the general formula (I), wherein Q+ represents either: (i) a cation having the formula (II), wherein $R_1$, $R_2$, $R_3$ and $R_4$ which may be the same or different, represent an alkyl radical having from 1 to 20 atoms of carbon, an aryl radical or an aralkyl radical, the number of atoms of carbon in $R_1+R_2+R_3+R_4$ being at least equal to 13 and preferably between 15 and 22, or: (ii) a polymer matrix carrying functions of formula (III), wherein: $R_5$, $R_6$ and $R_7$, which may be the same or different, represent a lower alkyl radical having from 1 to 6 atoms of carbon and n is a mean value comprised between 1.5 and 2.5, preferably between 1.8 and 2.1. Utilization for the fluoridation of acetylenic compounds mono or biactivated by addition of HF and for the preparation of organofluorinated compounds by nucleophilic substitution.

12 Claims, No Drawings

FLUORIDATION AGENT FOR ORGANIC COMPOUNDS, ESPECIALLY ACETYLENIC COMPOUNDS, THE PROCESS FOR THEIR PREPARATION AND THEIR USE IN ADDITION OR NUCLEOPHILIC SUBSTITUTION REACTIONS

The object of this invention is a new category of fluoridation agents for organic compounds, especially acetylenic compounds, the process for their preparation and their utilization in addition or nucleophilic substitution reactions.

Organo-fluorine compounds present great interest, especially fluorovinyl compounds, including certain of them, such as fluorofumarate and its derivatives, which demonstrate appreciable fungicidal properties.

In addition, fluorovinyl compounds constitute valuable intermediaries which can serve as base products for various syntheses, especially for fluorine polymer synthesis.

Preparations proposed up to this time for fluorovinyl compounds are particularly long and thus are not economical.

To date, no fluoridation agent has been described as being suitable for HF addition with acetylenic compounds and thus leading solely to fluoro-olefins.

Indeed, known fluoridation agents such as hydrogen fluoride (HF) liquid, whose implementation, moreover, is especially delicate, as well as other reagents such as such as G. A. OLAH's reagent (pyridine, 10 HF) J. Org. Chem. (1979), 44 (22) 3872, whose reactivity is very similar to that of liquid HF, produces saturated fluorine derivatives coming from the bis-addition of HF.

It was also proposed by ZUPAN et al Journal of Fluorine Chemistry, 24 (1984) 291–302, to use HF carrying resins as fluoridation agents. Such resins are particularly difficult to use because their preparation requires the use of liquid HF and these resins, when applied to acetylenic compounds, do not produce fluorovinyl compounds.

As the result of work on hydrogenofluoride ions, it was noted that [F$^-$,nHF] type ions with n$\simeq$2, which will henceforth be termed "dihydrogenotrifluoride" or "H$_2$F$_3^-$", appear to be a good source of HF.

Studies conducted have indeed allowed it to be demonstrated that dihydrogenotrifluoride anions allowed the addition of HF with bi-activated or mono-activated triple bonds, thus producing mono-fluorine ethylenic compounds with good yields, and that they could also lead to nucleophilic substitution reactions.

Moreover, in a relatively surprising and unexpected manner, it was noted that, compared with certain known fluoridation agents, dihydrogenotrifluoride anions did not lead to HF addition in activated or non-activated ethylenic compounds.

This invention has the object, in the capacity of a new industrial product, a fluoridation agent, especially for acetylenic compounds, with said fluoridation agent corresponding to the following general formula:

$$Q^+[F^-, nHF] \qquad (I)$$

in which:

Q+ represents either: (i) a cation having the formula:

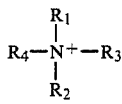

in which:

R1, R2, R3 and R4, identical or different, represent an alkyl radical having 1 to 20 carbon atoms, an aryl radical or an aralkyl radical, with the number of carbon atoms in R1+R2+R3+R4 being at least equal to 13 and preferably between 15 and 22, or: (ii) a polymeric matrix carrying functions having the formula:

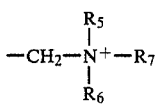

in which:

R5, R6 and R7, identical or different, represent a lower alkyl radical having from 1 to 6 carbon atoms, and n is an average value between 1.5 and 2.5, preferably between 1.8 and 2.1.

As can be noted from the above formula, the number "n" of compounds having formula (I) is around 2, such that, for purposes of simplification, these compounds will henceforth be termed "dihydrogenotrifluorides".

"Dihydrogenotrifluorides" such as defined above present the advantage with respect to known agents of allowing HF addition with activated triple bonds and thus producing fluorovinyl compounds in a simple and economical manner.

This selectivity with respect to acetylenic bonds is completely remarkable and thus allows the production of different fluorovinyl compounds which, up to the present, could be obtained only at the price of especially long and low-yield syntheses.

Moreover, compared with known fluoridation agents, the agents in accordance with the invention are easily obtained, without resorting to the use of liquid hydrogen fluoride (HF), which is especially significant, taking account of the danger and special conditions for the handling of this compound.

In accordance with a first embodiment of the invention, the fluoridation agent can be represented by the following formula:

in which:

R1, R2, R3 and R4, identical or different, represent an alkyl radical having from 1 to 20 carbon atoms, a phenyl radical or a benzyl radical, with the total number of carbon atoms of the R1+R2+R3+R4 radicals being at least equal to 13 and preferably between 15 and 22.

and n is between 1.5 and 2.5 and preferably between 1.8 and 2.1.

Among the dihydrogenotrifluorides corresponding to formula (II) above which are suitable for use as fluoridation agents, especially for acetylenic compounds, one can cite especially, without this list being limitative: tetrabutylammonium dihydrogenotrifluoride, tetrapentylammonium dihydrogenotrifluoride,
tetrahexylammonium dihydrogenotrifluoride,
hexadecyltrimethylammonium dihydrogenotrifluoride, and
benzyltriethylammonium dihydrogenotrifluoride.

Especially interesting results were observed when the fluoridation agent is tetrabutylammonium dihydrogenotrifluoride.

Various ammonium dihydrogenotrifluorides having formula (II) present a good solubility in low-polarity organic media, especially in chlorine-containing solvents such as chloroform, carbon tetrachloride, dichloromethane ou dichloro-1,2 ethane, which facilitates their use not only in addition reactions, but also those of nucleophilic substitution.

As this emerges from formula (II) above, the number of carbon atoms of the cation must be sufficiently high to produce a good degree of solubility in organic solvents.

Indeed, it has been observed that, when the number of carbon atoms was under about 13, the compounds presented a certain solubility in water and poor solubility in low-polarity or medium-polarity solvents.

In accordance with a second embodiment of the invention, the fluoridation agent according to the invention can be shown by the following formula:

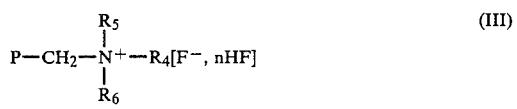

in which:

R4, R5 and R6, identical or different, represent a lower alkyl radical having from 1 to 6 carbon atoms and in which P represents a polymeric matrix, especially of the polystyrene-divinylbenzene type, and n is between 1.5 and 2.5, preferably between 1.8 and 2.1.

The polymeric matrices of the polystyrene divinylbenzene type are encountered especially in anion exchanging resins. On this subject, one can cite, as resins of this type, the Amberlyst A 26 and Amberlite IRA 900 resins.

Various studies conducted using these dihydrogenotrifluoride anion carrying resins allowed it to be shown that they could produce results entirely comparable to the compounds having formula (II) and that, in addition, they presented the great interest of being easily eliminated by filtration after the reaction and recycled.

This invention also has as an object the process for the preparation of ammonium dihydrogenotrifluorides having formula (II).

This process, which is done in accordance with the phase transfer technique, consists of causing the reaction of an organic phase, comprised of a medium-polarity solvent, such as dichloromethane or dichloro-1,2 ethane, containing an ammonium fluoride having the fomula:

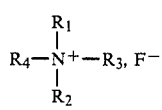

in the presence of a saturated aqueous phase of a mixture of aqueous hydrogen fluoride and an alkaline fluoride, or an alkaline hydrogenodifluoride, with the molar ratio of the constituents of the aqueous phase with respect to the ammonium fluoride being between about 4 and 6.

The concentration of ammonium fluoride in the organic phase is of particular importance, such that the number n remains within the values mentioned above, i.e., between 1.5 and 2.5 and preferably between 1.8 and 2.1.

Preferably, the concentration of ammonium fluoride must be between 0.08 and 0.12 moles per liter of solvent.

The alkaline salts of the aqueous phases are preferably those of potassium or sodium. The alkaline hydrogenodifluoride can also be replaced by ammonium hydrogenodifluoride.

As was mentioned above, this process, with respect to known processes, presents the great advantage of not requiring the utilization of liquid HF, which is especially delicate and dangerous to handle, but rather of an aqueous HF solution, preferably 50%.

The reaction time is generally between about 1 and 3 hours; the aqueous phase is subsequently decanted and the organic phase is collected; it is then heated under surrounding pressure so as to eliminate the water contained therein by "water-organic solvent" azeotropic distillation.

The product which is obtained is most often in viscous form, containing a certain proportion of solvent, though the latter is not an impediment to the subsequent fluoridation reactions.

The initial ammonium fluorides can be prepared in accordance with the method described by H. KOBLER et al. Leibigs Ann. Chem. (1978) 1937 according to the following reactive chart:

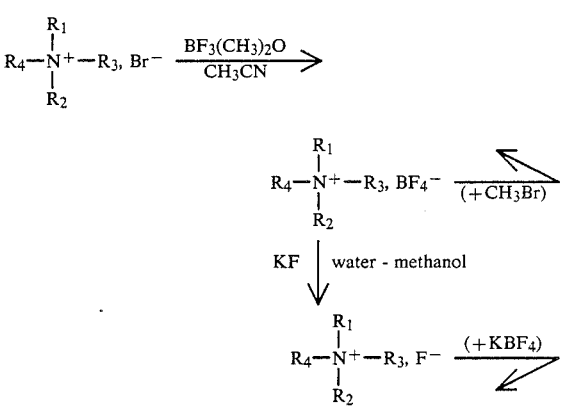

The process for the preparation of dihydrogenotrifluoride anion carrying resins consists of treating an ion exchanging resin such as an Amberlyst A 26 or Amberlite IRA 900 resin in Cl⁻ form with soda, then with an aqueous HF solution, in order to put it into F⁻ form.

The resin in F⁻ form is then treated as described above and in the same molar ratio, with a saturated aqueous solution of a mixture of aqueous hydrogen fluoride and an alkaline fluoride or an alkaline or ammonium hydrogenodifluoride.

After agitation at room temperature for about 5 to 8 hours, the resin is filtered, then washed.

This invention also has the object of a process for the preparation of fluorovinyl compounds from mono-activated or bi-activated acetylenic compounds accordance with the following reactive chart:

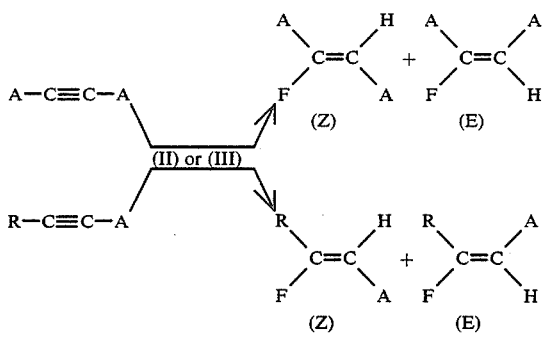

A = represents an activating function
and R = alkyl, aryl or aralkyl.

This process consists of putting into contact a mono or bi-activated acetylenic compound in the presence of a fluoridation agent such as defined above, at a temperature between room temperature and about 120 degrees C. and for a time period between 3 and 50 hours.

The fluoridation agent is generally utilized in a molar excess of about 1.5 to 3 and preferably about 2 with respect to the acetylenic compound.

Preferably, the reaction is conducted in the presence of a low-polarity or medium-polarity organic solvent, in order to render the acetylenic compound soluble, but can possibly be conducted without solvent when the fluoridation agent is an ammonium dihydrogenotrifluoride having formula (II).

As an inert solvent with respect to the fluoridation agent and the acetylenic substratum, preferably, a chlorine containing solvent such as dichloromethane, dichloro-1,2 ethane, carbon tetrachloride or chloroform, or an aliphatic hydrocarbon such as n-octane is utilized.

After the end of the reaction and possible cooling, the reactive medium is treated with water and extracted with ether, or is simply filtered when the fluoridation agent is a dihydrogenotrifluoride anion carrying resin.

As indicated above, the HF addition is stopped at the ethylenic stage, with the possible mixture of stereo-isomers (Z) and (E) being a function of the fluoridation agent and the initial acetylenic substratum.

With respect to ammonium dihydrogenotrifluorides (II), the utilization of dihydrogenotrifluoride anion carrying resins seems to more clearly promote HF syn-addition.

The table below highlights this property when one utilizes on the one hand, tetrabutyl ammonium dihydrogenotrifluoride $(C_4H_9)N^+$, $H_2F_3^-$ and, on the other hand, an $H_2F_3^-$ anion carrying Amberlyst A 26 resin.

| Flourine compound | $(C_4H_9)_4N^+H_2F_3^-$ | | Amberlyst A26 $H_2F_3^-$ | |
|---|---|---|---|---|
| | isomer Z | isomer E | iso-mer Z | iso-mer E |
| $CH_3O_2C-CF=CH-CO_2CH_3$ | 100 | 0 | 81 | 19 |
| $NC-CF=CH-CN$ | 63 | 37 | 68 | 32 |
| $C_7H_{15}-CF=CH-CN$ | 70 | 30 | 33 | 67 |
| $C_6H_5-CF=CH-CN$ | 80 | 20 | 72 | 28 |
| $C_4H_9-CF=CH-CO_2CH_3$ | 42 | 58 | 35 | 65 |
| $C_6H_5-CF=CH-CO_2CH_3$ | 95 | 5 | 88 | 12 |
| $C_6H_5-CF=CH-CH=O$ | 91 | 9 | 83 | 17 |

In addition, it must be noted that no appreciable difference was observed in the yields in the utilization of these two types of fluoridation agents.

Although more specifically, reference was made to the HF addition properties with acetylenics, the fluoridation agents in accordance with the invention also form compounds which are especially valuable for producing organo-fluoridated compounds by nucleophilic substitution by the $F^-$ anion on sp3 carbon.

In particular, the $H_2F_3^-$ carrying resins are seen to be good fluoridation agents for α-bromo ketones and α-bromo esters; substitution rates are generally very good and are obtained under moderate conditions.

Completely similar reactions were also observed using non-activated compounds.

Several examples will now be provided in an illustrative and non-limitative capacity, of the preparation of fluoridation agents in accordance with the invention along with examples for the fluoridation of acetylenic compounds.

EXPERIMENTAL SECTION

A. Preparation of Tetrabutylammonium Dihydrogenotrifluoride $(C_4H_9)_4N^+$, $H_2F_3^-$ (1) Preparation of tetrabutylammonium fluoride $(C_4H_9)_4N^+F^-$ 1.8 g (0.031 mole) of KF dissolved in 6 ml of water are added to 9.9 g (0.03 mole) of $(C_4H_9)_4N^+BF_4^-$, prepared in accordance with H. Kobler et al., Leibigs Ann. Chem. (1978), 1937, dissolved in 20 ml of methanol. All of the $BF_4^-$ ions are pulled into $KBF_4$, which precipitates and is filtered, then washed with a small amount of methanol. The majority of the methanol and water is next eliminated by evaporation under a jet vacuum pump at 40 degrees C. for about one half hour. A slightly viscous liquid residue of the desired product along with a small amount of water and methanol is obtained, which is utilized as it is for the following phase transfer reaction.

It is not desirable to totally eliminate the residual water, because this could cause the product to decompose.

(2) Preparation of tetrabutylammonium dihydrogenotrifluoride $(C_4H_9)N^+$, $H_2F_3^-$ 0.03 mole of $(C_4H_9)_4N^+F^-$ as prepared above is dissolved in 300 ml of dichloro-1,2 ethane (DCE). To this organic solution contained in a polyethylene flask, one adds a saturated aqueous solution either of an HF-KF mixture in the proportions of 12 g of 50% (0.3 mole) aqueous HF+8.7 g of KF (0.15 mole) and 23 ml of water, or an $HF-KF_2$ mixture in the proportions of 6 g of 50% (0.15 mole) aqueous HF+11.7 g of $KHF_2$ (0.15 mole) and 35 ml of water.

The heterogeneous mixture of these two organic and aqueous phases is left under agitation at room temperature for about two hours. After the aqueous phase is decanted, the organic phase which is collected is heated under surrounding pressure so as to eliminate the water contained therein by azeotropic distillation (water-DCE); subsequently, the majority of the remaining DCE is finally evaporated under a vacuum.

The viscous tetrabutyl ammonium dihydrogenotrifluoride residue obtained contains about 15% by weight of DCE, the presence of which does not constitute any impediment for the fluoridation reactions.

By accelerated evaporation of the DCE, one obtains a sample of tetrabutylammonium dihydrogenotrifluoride, the elementary analysis of which produces the following results:

Cal.: C%, 63.74; H%, 12.7; N%, 4.65; F%, 18.91; Found 61.56; 12.13; 4.42; 18.64;

Acid-base quantitative analysis

The quantitative analysis of the residue conducted with soda in the presence of phenolphthalein allows the mole number n of fixed HF's per mole of $(C_4H_9)_4N^+F^-$ to be derived. This number is, on the average, between 1.9 and 2.1 (with this calculation taking into account the residual quantity of DCE, which is difficult to eliminate completely and is evaluated by RMN$^1$H).

NMR spectrum

In NMR'H, the spectrum of a sample of residue obtained, dissolved in CDCl$_3$, provides, in addition to the characteristic signals of the $(C_4H_9)_4N^+$ group:

A very fine singlet having $\delta = 3.8$ ppm, which can be attributed to the DCE, A singlet of average width ($\Delta\nu$ at mid-height $\sim 5H_z$) in the region of the low fields which, regardless of the sample, are characterized by an average intensity of 1.9–2.1 H nucleii and by an average chemical displacement $\delta = 12.9$ ppm (concentration$\simeq$1.5–2 mol.l$^{-1}$). In NMR$^{19}$F, a singlet having $\delta = -167$ ppm (measured with respect to CFCL$_3$) is noted.

Infrared spectrum

The IR spectrum presents absorption bands which can be attributed respectively to the combination (2560 cm$^{-1}$ and 2320 cm$^{-1}$ elongation (1800 cm$^{-1}$) and bending (1155 cm$^{-1}$, 1115 cm$^{-1}$ and 1060–1050 cm$^{-1}$) vibrations which are characteristic of the H$_2$F$_3^-$ anion.

PREPARATION OF FLUOROVINYL COMPOUNDS FROM MONO AND BI-ACTIVATED ACETYLENIC COMPOUNDS THROUGH THE USE OF TETRABUTYLAMMONIUM DIHYDROGENOTRIFLUORIDE $(C_4H_9)_4N^+H_2F_3^-$ (1) Mono-activated acetylenics General mode of operation 0.015 mole of acetylenic compound and 0.03 mole of tetrabutylammonium dihydrogenotrifluoride are placed in a 50 ml flask. The flask is corked, the reactive mixture is heated under agitation in an oil bath which is thermostatically controlled at 110 or 120 degrees C., depending on the case. The reactive medium is next treated with water, extracted with ether; the ether phase is next washed with water and dried on anhydrous sodium sulfate. After the ether is evaporated, the residue is purified by distillation. Thus the adduct or a mixture of stereo-isomer adducts (Z) and (E) is obtained.

According to the operating method above, the following acetylenic compounds have been treated:

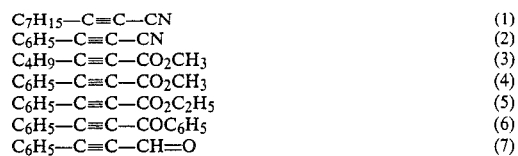

| | | (1) |
|---|---|---|
| $C_7H_{15}-C\equiv C-CN$ | | (1) |
| $C_6H_5-C\equiv C-CN$ | | (2) |
| $C_4H_9-C\equiv C-CO_2CH_3$ | | (3) |
| $C_6H_5-C\equiv C-CO_2CH_3$ | | (4) |
| $C_6H_5-C\equiv C-CO_2C_2H_5$ | | (5) |
| $C_6H_5-C\equiv C-COC_6H_5$ | | (6) |
| $C_6H_5-C\equiv C-CH=O$ | | (7) |

The results obtained with respect to fluorovinyl compounds are shown in the following table:

| COMPOUNDS OBTAINED | Temperature (°C.) | Length of reaction (h) | Global rate of transformation (%) | Relative proportions of stereo-isomers Z | E |
|---|---|---|---|---|---|
| (1')$C_7H_{15}-CF=CH-CN$ | 110 | 7 | 95 | 70 | 30 |
| (2')$C_6H_5-CF=CH-CN$ | 110 | 8 | 80 | 80 | 20 |
| (3')$C_4H_9-CF=CH-CO_2CH_3$ | 120 | 24 | 90 | 42 | 58 |
| (4')$C_6H_5-CF=CH-CO_2CH_3$ | 120 | 21 | 75 | 95 | 5 |
| (5')$C_6H_5-CF=CH-CO_2C_2H_5$ | 120 | 24 | 45 | 82 | 18 |
| (6')$C_6H_5-CF=CH-CO-C_6H_5$ | 110 | 50 | 53 | 100 | 0 |
| (7')$C_6H_5-CF=CH-CHO$ | 100 | 4.5 | 75 | 91 | 9 |

The characteristics of the fluorovinyl compounds obtained 1' to 7' are as follows:

(1') Fluoro-3 decene-2 nitrile (Z+E)

Eb$_{20}$ = 113°–133° C. – R$^{dt}$ 84%.

Analysis: C$_{10}$H$_{16}$FN: Calc: C%, 70.97; H%, 9.53; F%, 11.23; N%, 8.28; Found: 70.99; 9.54; 10.79; 7.91.

(2') Fluoro–3 phenyl–3 propene–nitrile (Z+E)

Eb$_{10}$ = 100°–128° C. – R$^{dt}$ 70%.

Analysis: C$_9$H$_6$FN: Calc: C%, 73.46; H%, 4.11; F%, 12.91; N%, 9.52; Found: 73.26; 4.16; 12.79; 9.66.

(3') Mixture of fluoro-3 heptene-2 methyl oate C$_4$H$_9$—CF=CH—CO$_2$CH$_3$ (Z+E) and of fluoro 3-heptene-3 methyl oate C$_3$H$_7$—CH=CF—CH$_2$—CO$_2$CH$_3$ (Z+E) (relative prop. 5/3): Eb$_{21}$ = 67–84° C.

Mass spectrum: C$_8$H$_{13}$FO$_2$—(M+): Calc: 160.089950; Tr.: 160.0894. (4') Fluoro-3 phenyl-3 methyl propanoate (Z+E)

Eb$_{1,5}$ = 113°–116° C. – R$^{dt}$ 67%.

Mass spectrum: C$_{10}$H$_9$FO$_2$ (M+): Calc: 180.058652; Found: 180.0588.

(5') Fluoro-3 phenyl-3 ethyl propanoate (Z+E) (characterized by IR and NMR, but not isolated)

(6') Diphenyl-1,3 fluoro-3 propenone (Z)

F = 61 degrees C.

This stereo-isomer Z was obtained pure after chromatography of the reactive mixture on silicon gel (elutant: Hexane-Benzene (70/30).

Analysis: C$_{15}$H$_{11}$FO-Calc: C%, 79.63; H%, 4.90; Found: 79.57; 4.98. (7') Fluoro-3 phenyl-3 propenal (Z+E)

Eb$_{0,7}$ = 83° C. – R$^{dt}$ 61%

From this distilled mixture, the stereo-isomer (Z) was obtained pure by the washing with methane of mixture (Z+E): one thus obtains a well-crystallized solid F = 32 degrees C.

Mass spectrum: C$_9$H$_7$FO: (M+): Calc.: 150.048089; Found: 150.0482.

The latter compound can be oxidized easily in fluoro-3 phenyl-3 propenoic acid $C_6H_5$—CF=CH—COOH, which was characterized in mass spectrometry:

$C_7H_7FO_2$: (M+-H): Calc: 165.0334; Found: 165.0352.

(2) Bi-activated acetylenics

The following acetylenic compounds:

$CH_3O_2C$—C≡C—$CO_2CH_3$ (8)
$C_6H_5CO$—C≡C—$COC_6H_5$ (9)
CN—C≡C—CN (10)

treated under the conditions defined below produced the following results with respect to fluorovinyl compounds:

| COMPOUNDS OBTAINED | Temperature (°C.) | Length of reaction (hours) | Global rate of transformation | Relative proportions of stereo-isomers Z | E |
|---|---|---|---|---|---|
| (8') $CH_3O_2C$—CF=CH—$CO_2CH_3$ | 60 | 9 | 90 | 100 | 0 |
| (9') $C_6H_5$—CO—CF=CH—CO—$C_6H_5$ | 60 | 24 | 57 | 100 | 0 |
| (10') NC—CF=CH—CN | 25 | 3 | 85 | 65 | 35 |

Preparation of the compound having the formula:

$CH_3O_2C$—CF=CH—$CO_2CH_3$ (8')

0.015 mole of acetylene methyl dicarboxylate (8) is added to 0.03 mole of tetrabutylammonium dihydrogenotrifluoride in a 50 ml flask. The flask containing this mixture, which forms a homogeneous solution, is corked and heated under magnetic agitation in an oil bath thermostatically controlled at 60 degrees C. A rapid blackening of the reactive medium is immediately noted when the mixture is formed. NMR'H analyses of samples allow the course of the reaction to be monitored. After 9 hours of heating at 60 degrees C., the attachment of an HF equivalent to the acetylenic bond appears quasi-total and there is no further change in the reaction.

After cooling, the reactive medium is treated with water and extracted with ether. The ether phase is washed several times with water to a pH of approximately 5-6 and is dried on anhydrous sodium sulfate. After the ether is evaporated, the methyl fluorofumarate (Z) (8') is collected and purified by distillation ($Eb_{10-11}$=92 degrees C.) or by recrystallization in a petroleum ether-ether mixture (melting point 46 degrees C.) Yield=75%.

Elementary analysis $C_6H_7FO_4$: Calc: C%, 44.45; H%, 4.35; F%, 11.71; Found: 44.52; 4.36; 10.76;

Preparation of the compound having the formula:

$C_6H_5$—CO—CF=CH—CO—$C_6H_5$ (9')

0.03 mole of tetrabutylammonium dihydrogenotrifluoride is added to 0.015 mole of acetylenic diketone (9) dissolved in 15 ml of dichloro-1,2 ethane. This homogeneous mixture is heated under agitation in a 50 ml flask, equipped with a reflux coolant over which a calcium chloride tube is attached, for 24 hours, in an oil bath thermostatically controlled at 60 degrees C.

After cooling, the mixture is first extracted with ether, then washed with water and dried on anhydrous sodium sulfate. After the solvents are evaporated, a mixture of the initial diketone (9) and the desired adduct is collected.

These two compounds can be separated only be chromatography on silicon (elutant: hexane-dichloromethane in the proportions of 80/20). One thus obtains the desired fluorine diketone in the form of a pale yellow solid with melting point: 62 degrees C.

Elementary analysis: $C_{16}H_{11}FO_2$: Calc: C%, 75.58; H%, 4.36; F%, 7.47; Found: 75.55; 4.45; 7.00;

(3) Preparation of the compound having the formula:

NC—CF=CH—CN (10')

1 g (0.013 mole) of acetylene dinitrile (10) is dissolved in 20 ml of dichloro-1,2 ethane. To this solution, at room temperature, 0.026 mole of tetrabutyl ammonium dihydrogenofluoride is added at once. The reactive mixture immediately blackens and heats up abruptly (the temperature reaches about 40 degrees C.). This mixture is next left under agitation at room temperature for 3 hours. Then, as in the above, it is treated with ether, then with water, and the ether phase is washed with water and dried on anhydrous sodium sulfate. After the solvents are evaporated, a residue is collected, in which the stereo-isomer adducts (Z) and (E) are perfectly characterized by mass spectrometry and by NMR.

Mass spectrum: $C_4HFN_2$—(M+): Calc.: 96.012374; Found: 96.0126.

B—PREPARATION OF AMBERLYST A 26 AND AMBERLITE IRA 900 H2F3 ANION CARRYING RESINS

Commercial Amberlyst A 26 and Amberlite IRA 900 resins are found in CL− form.

In a first stage, they are transformed into F− form according to the method described by Colonna et al. J. Chem. Soc. Perkin I, (1979), 2248, i.e., by two successive washes, the first with dilute (≃1N) soda; the second with an aqueous HF solution (≃1N).

50 g of Amberlyst A26 or Amberlite IRA 900 resin in F− form, which corresponds to about 0.1 mole of anion, are placed in a polyethylene vessel with an aqueous solution comprised either of 20 g of an aqueous 50% HF (0.5 mole) solution+39 g (0.5 mole) of $KHF_2$+115 ml of water, or 40 g of an aqueous solution of 50% HF (1 mole)+29 g (0.5 mole) of KF+70 ml of water.

After mixing at room temperature for 8 hours, the resin is filtered and washed with acetone to remove the majority of the water contained therein, then with ether. The dry resin obtained still contains a small amount of water, and is added to 400 ml of dichloro 1,2-ethane (DCE). The remaining water is then removed by water+DCE azeotropic distillation.

After filtration and air drying, the resin is finally collected and utilized as it is in subsequent reactions.

Characteristics of the resins obtained

The ionic exchange capacity of these resins in dry matter is, on the average, according to literature, 3.8 meq $g^{-1}$ in Cl− form.

In order to evaluate the number n of moles of HF transferred, one has first of all determined, according to G. Cainelli et al. Synthesis (1976) 472, the exchange capacity for these resins (dry matter) in OH⁻ form by an acid-base quantitative analysis with sulfuric acid.

Next, upon completion of the treatment of the F⁻ form to reach the (F⁻, n HF) form, the acidity of the latter form was measured using soda in the presence of phenol phthalein.

The results obtained are as follows:

| Resin | OH⁻ form number of meq g⁻¹ | [F⁻, nHF⁻] form number of meq g⁻¹ | n |
|---|---|---|---|
| Amberlyst A 26 | 4.0–4.1 | 6.7–6.9 | 1.95–2.04 |
| Amberlite IRA 900 | 4.0–4.2 | 6.9–3.2 | 1.95–2.05 |

The value of the number n is determined as a function of the following considerations:

(a) based on the results ensuing from the quantitative analysis of the resins in OH⁻ form, one can derive, for each resin, a molar mass associated with an OH⁻ ion equivalent. One thus finds M=223–236 g for the Amberlyst A 26 resin and M=221–223 g for the Amberlite IRA 900 resin.

(b) it is admitted that the OH⁻ form is next completely neutralized by HF, such that the quantitative analysis of the [F⁻, n HF] forms can be conducted using the imaginary molar massvalues found above. Thus, one obtains an appropriate and highly reproducible assessment of the number n which is sought, which, for these resins, on the average, is from 1.9 to 2.1.

evaporated, the residue is NMR′H analyzed to determine the global yield of the HF dilution as well as the relative proportions of stereo-isomers. Next, the fluorovinyl compounds obtained are purified by distillation of the residue.

The fluorovinyl compounds are identified perfectly by their physical constants and their spectroscopic parameters by comparison with the values previously determined upon completion of the reactions with tetrabutylammonium dihydrogenotrifluoride.

According to the operating mode described above, the following components were thus treated:

$C_7H_{15}—C≡C—CN$     (1)
$C_6H_5—C≡C—CN$     (2)
$C_4H_9—C≡C—CO_2CH_3$     (3)
$C_6H_5—C≡C—CO_2CH_3$     (4)
$C_6H_5—C≡C—CH=O$.     (7)

The results obtained in fluorovinyl compounds are grouped together in the following table:

| COMPOUNDS OBTAINED | Temp. (°C.) | Length of reaction (hours) | Global rate of transformation % | Relative proportions of stereo-isomers Z | E |
|---|---|---|---|---|---|
| (1′)$C_7H_{15}$—CF=CH—CN | 110 | 30 | 95 | 33 | 67 |
| (2′)$C_6H_5$—CF=CH—CN | 110 | 20 | 88 | 72 | 28 |
| (3′)$C_4H_9$—CF=CH—$CO_2CH_3$ | 110 | 16 | 78 | 35 | 65 |
| (4′)$C_6H_5$—CF=CH—$CO_2CH_3$ | 120 | 24 | 85 | 88 | 12 |
| (7′)$C_6H_5$—CF=CH—CH=O | 110 | 4 | 62 | 83 | 17 |

(2) Bi-activated acetylenics
The following acetylenic compounds:

$CH_3O_2C—C≡C—CO_2CH_3$     (8)
$CN—C≡C—CN$     (10)

treated under the conditions described below produced the following results with respect to fluorovinyl compounds:

| COMPOUNDS OBTAINED | Temp. (°C.) | Length of reaction (hours) | Global rate of transformation % | Stereo-isomers Z | E |
|---|---|---|---|---|---|
| (8′)$CH_3O_2C$—CF=CH—$CO_2CH_3$ | 60 | 30 | 80 | 81 | 19 |
| (10′)NC—CF=CH—CN | 25 | 7 | 87 | 68 | 32 |

PREPARATION OF FLUOROVINYL COMPOUNDS FROM MONO AND BI-ACTIVATED ACETYLENIC COMPOUNDS THROUGH THE USE OF AMBERLYST A 26 AND AMBERLITE IRA 900 HAVING $H_2F_3^-$ ANIONS.

(1) Mono-activated acetylenics

General operating method

To a 50 ml flask containing 0.015 mole of acetylenic compound dissolved in 20 ml of n-octane, one adds 9 g of Amberlyst A 26 or Amberlite IRA 900 $H_2F_3^-$ anion carrying resin, as obtained above. The flask is equipped with a reflux coolant mounted over a calcium chloride tube, and the reactive medium is heated under agitation in an oil bath which is thermostatically controlled at 110–120 degrees.

After the reactive medium is cooled, the resin is filtered and washed with ether. After the solvents are Preparation of the compound having the formula:

$CH_3O_2C—CF=CH—CO_2CH_3$

In a 50 ml flask, one successively adds 0.015 mole (2.1 g) of methyl acetylene dicarboxylate, 8.8 g of Amberlyst A 26 $H_2F_3^-$ anion carrying resin, such as is obtained above (which is equivalent to about 0.03 mole of $H_2F_3^-$) and 10 ml of carbon tetrachloride. The flask is equipped with a reflux coolant over which a $CaCl_2$ tube is mounted, and the reactive medium is heated in an oil bath thermostatically controlled at 60 degrees C. The reaction is followed by NMR′H sample analysis. When the reaction is completed, the resin is filtered and washed with ether; the solvents are next evaporated so that the desired product can be collected (1.7 or a yield of 70%).

NMR SPECTRUM of the stereo-isomer (E)

NMR′:=CH: δ=6.09 (d)−³JHF=16.0 Hz;
19F:=CF: δ=−109.4 (d)−³JHF=15.7 Hz.
Preparation of the compound having the formula:

$$NC-CF=CH-CN$$

1 g (0.013 mole of acetylene dinitrile is dissolved in 20 ml of carbon tetrachloride. To this solution in a 50 ml flask, one adds 7.7 g of Amberlyst A 26 $H_2F_3^-$ anion carrying resin. The flask is corked, then the mixture is left under agitation at room temperature for 7 hours. The resin is washed, then filtered with ether and the solvents are evaporated.

Thus, a residue is collected, which contains a mixture of stereo-isomers (E) and (Z) which are characterized perfectly by their NMR spectra.

We claim:
1. A fluoridation agent having the formula:

$$Q^+[F^-, nHF]$$

wherein $Q^+$ represents (i) a cation having the formula:

$$R_4-\overset{R_1}{\underset{R_2}{N^+}}-R_3$$

wherein $R_1$, $R_2$, $R_3$ and $R_4$ each independently represent alkyl having 1-20 carbon atoms, aryl or aralkyl, wherein the number of carbon atoms in $R_1+R_2+R_3+R_4$ is at least equal to 13, or (ii) a polymeric matrix carrying functions having the formula:

$$-CH_2-\overset{R_5}{\underset{R_6}{N^+}}-R_7$$

wherein $R_5$, $R_6$ and $R_7$ each independently represent lower alkyl having 1-6 carbon atoms, and
n has an average value ranging from 1.5 to 2.5.

2. The fluoridation agent of claim 1 wherein the number of carbon atoms in $R_1+R_2+R_3+R_4$ ranges from 15-22.

3. The fluoridation agent of claim 1 wherein n has an average value ranging from 1.8 to 2.1.

4. The fluoridaiton agent of claim 1 having the formula $$R_4-\overset{R_1}{\underset{R_2}{N^+}}-R_3[F^-, nHF]$$

wherein $R_1$, $R_2$, $R_3$ and $R_4$, each independently, represent alkyl having 1-20 carbon atoms, phenyl or benzyl, wherein the total number of carbon atoms in $R_1+R_2+R_3+R_4$ is at least equal to 13, and
n ranges from 1.5 to 2.5.

5. The fluoridation agent of claim 4 wherein the number of carbon atoms in $R_1+R_2+R_3+R_4$ ranges from 15 to 22.

6. The fluoridation agent of claim 4 wherein n ranges from 1.8 to 2.1.

7. The fluoridation agent of claim 1 selected from the group consisting of
tetrabutylammonium dihydrogenotrifluoride,
tetrapentylammonium dihydrogenotrifluoride,
tetrahexylammonium dihydrogenotrifluoride,
hexadecyltrimethylammonium dihydrogenotrifluoride, and
benzyltriethylammonium dihydrogenotrifluoride.

8. The fluoridation agent of claim 1 which is tetrabutylammonium dihydrogenotrifluoride.

9. The fluoridation agent of claim 1 having the formula $$P-CH_2-\overset{R_5}{\underset{R_6}{N^+}}-R_4[F^-, nHF]$$

wherein $R_4$, $R_5$ and $R_6$ each independently represent lower alkyl having 1-6 carbon atoms,
P represents a polymeric matrix and
n ranges from 1.5 to 2.5.

10. The fluoridation agent of claim 9 wherein n ranges from 1.8 to 2.1.

11. The fluoridation agent of claim 9 wherein the polymeric matrix is of the polystyrene divinyl benzene type.

12. A fluoridation agent having the formula $$P-CH_2-\overset{R_5}{\underset{R_6}{N}}-R_4[F^-.nHF]$$

wherein $R_4$, $R_5$ and $R_6$ each independently represent lower alkyl having 1-6 carbon atoms,
P represents a polymer matrix of the polystyrene divinyl benzene type, and
n ranges from 1.5 to 2.5.

* * * * *